United States Patent
Yuan et al.

(10) Patent No.: US 10,160,989 B2
(45) Date of Patent: Dec. 25, 2018

(54) SYSTEM AND METHOD OF CO-CULTIVATING MICROALGAE WITH FUNGUS

(75) Inventors: Joshua (Shuhua) Yuan, College Station, TX (US); Shangxian Xie, College Station, TX (US)

(73) Assignee: RENEWUEL LLC, College Station, TX (US)

( * ) Notice: Subject to any disclaimer, the term of this patent is extended or adjusted under 35 U.S.C. 154(b) by 743 days.

(21) Appl. No.: 13/346,426

(22) Filed: Jan. 9, 2012

(65) Prior Publication Data

US 2012/0282651 A1    Nov. 8, 2012

Related U.S. Application Data

(60) Provisional application No. 61/481,721, filed on May 2, 2011.

(51) Int. Cl.
| | |
|---|---|
| *C12P 39/00* | (2006.01) |
| *C12N 1/12* | (2006.01) |
| *C12N 1/14* | (2006.01) |
| *C12P 1/02* | (2006.01) |
| *C12P 7/64* | (2006.01) |

(52) U.S. Cl.
CPC ............... *C12P 39/00* (2013.01); *C12N 1/12* (2013.01); *C12N 1/14* (2013.01); *C12P 7/6463* (2013.01)

(58) Field of Classification Search
None
See application file for complete search history.

(56) References Cited

U.S. PATENT DOCUMENTS

| | | | |
|---|---|---|---|
| 5,348,872 A | 9/1994 | Lin et al. | |
| 5,429,942 A * | 7/1995 | Kock .................... | C12P 7/6472 435/134 |
| 6,255,505 B1 * | 7/2001 | Bijl ......................... | A23D 9/00 435/132 |
| 2002/0039758 A1 * | 4/2002 | De Laat .................. | C12N 9/16 435/41 |
| 2008/0299257 A1 * | 12/2008 | Uchino ........................... | 426/60 |
| 2009/0004715 A1 * | 1/2009 | Trimbur et al. .............. | 435/166 |
| 2009/0246844 A1 * | 10/2009 | Khramtsov ............... | C12P 7/16 435/161 |
| 2010/0159557 A1 * | 6/2010 | Liu et al. ...................... | 435/174 |

(Continued)

OTHER PUBLICATIONS

Hiruta et al. "Application of Maxblend Fermentor® for microbial processes." 1997, J Ferment Bioeng 83(1): 79-86.

(Continued)

*Primary Examiner* — Renee Claytor
*Assistant Examiner* — Lauren K Van Buren
(74) *Attorney, Agent, or Firm* — Riverside Law LLP (57) ABSTRACT

One of the most important technical barriers for algal biofuel is the substantial harvesting and extracting cost. The present invention includes a system and method for the pelletization of single cell microalgae through co-cultivation with filamentous fungi to enable the low cost separation of microalgae from liquid medium and to significantly increase the biomass and lipid yield. The approach represents a simple and straightforward method to significantly reduce the cost for algae-based biofuel production and enable the economically viable algae biofuel production.

14 Claims, 8 Drawing Sheets

(56) References Cited

U.S. PATENT DOCUMENTS

2010/0279354 A1* 11/2010 de Crecy .................... 435/71.1

OTHER PUBLICATIONS

Singh et al., "Commercialization potential of microalgae for biofuels production" 2010, Renew Sust Energ Rev 14(9): 2596-2610.
Vansuijdam et al., "An inoculum technique for the production of fungal pellets." 1980, Eur J Appl Microbiol Biotechnol 10(3): 211-221.
Verma et al., "Studies on Pelleted Form of Growth Morphology Achieved by Aspergillus strains with Different Sugar Treatment Under Submerged Cultivation." 2009, J Pure & Appl Microbiol 3(2): 559-565.

* cited by examiner

SYSTEM AND METHOD OF CO-CULTIVATING MICROALGAE WITH FUNGUS

CROSS REFERENCE TO RELATED APPLICATIONS

This application claims the benefit of priority to U.S. Provisional Patent Application No. 61/481,721, filed on May 2, 2011, which is herein incorporated by reference in its entirety.

BACKGROUND OF THE INVENTION

Algae, especially microalgae, are a group of organisms that have received a great deal of interest during the current energy and fuel crisis, due in part to their relatively low cost to large biomass ratio. For example, it is believed that algae can produce as many as 30 times more biomass than land crops, per acre. Further to this, most algae can live in conditions having only water (untreated), a carbon source, and sunlight, as they produce their own energy for metabolism. Furthermore, because the fatty acid of algae can be extracted and used to generate biofuel (among other natural products and bioactive compounds) algae has been generally considered a renewable energy source with tremendous potential. Besides potential in biofuel, microalgae can be used to produce a variety of nutriceuticals including unsaturated fatty acid, pigment, antioxidant, surfactant, and others. In addition, genetically modified microalgae can be used to produce an even broader range of products, including therapeutic proteins, bioplastics, surfactant, terpenoid products, and others.

Algae can be grown in a variety of systems. For example, algae can be grown in both open-culture systems, such as ponds, lakes and raceways. The advantage of such systems is that they are generally cost-effective and easy to manage. Algae can also be grown in highly controlled closed-culture systems, similar to those used in commercial fermentation processes. However, closed-culture systems typically command higher investments and operating costs, but are independent of all variations in agro-climatic conditions and are very closely controlled for optimal performance and quality.

One of the major technical barriers for algae biofuel production is the considerable harvesting and extraction cost associated with the process for the separation of Single Cell Oleaginous (SCO) microalgae from liquid medium. For example, algae harvesting and lipid extraction steps alone can account for up to 50% of the total cost of algal biofuel production.

Current harvesting strategies include centrifugation, column flotation cross-flow microfiltration, electrolytic flocculation, and other such methods. However, all of these strategies have limitations when scaled up for commercialization. For example, the centrifugation of millions of gallons of liquid medium requires considerable energy input and prohibitively high production costs. Thus, the development of an effective harvesting strategy is crucial to reduce the cost of algae biofuel (Singh et al., 2010, Renew Sust Energ Rev 14(9): 2596-2610). The ability to integrate low cost harvesting with high yielding cultivation would therefore enable an economically viable algal biofuel production system. In addition, such technology can also reduce the cost for algae-based production of nutriceuticals like unsaturated fatty acids, antioxidants, surfactant, therapeutics, bioplastics, proteins, and other chemical products.

Filamentous fungi have been broadly used for the industrial production of various proteins, lipids and other therapeutics. For example, filamentous fungi like *Mortierella isabellina, Mucor circinelloides* and *Cunninghamella echinulata* have been used for SCO lipid production. In submerged cultivations, fungi can generally grow into two different morphologies, filamentous and pellet morphology, depending on culture conditions and medium compositions. The pellet morphology, as compared to filamentous morphology, can significantly decrease viscosity and enhance mixing and mass transfer, which can in turn greatly improve fermentation performance (Vansuijdam et al., 1980, Eur J Appl Microbial Biotechnol 10(3): 211-221). For example, Hiruta et al. reported that pelletization can lead to high yields of gamma-linolenic acid (GLA) by *Mortierella ramanniana* (Hiruta et al. 1997, J Ferment Bioeng 83(1): 79-86).

Despite the various advantages, the pelletization process is difficult to effectively control. For example, oxygen, pH and other factors can all impact the formation and size of the pellets as well as the fermentation performance. That said, attempts to optimize fungal pelletization for industrial applications have been made (Verma et al. 2009, J Pure & Appl Microbial 3(2): 559-565). Despite these attempts, pelletization has seldom been used for improving the fermentation performance in a co-cultivation setting, due in part to the challenges in optimizing a more complex system. In particular, pelletization has never been explored for green algae cultivation and processing. The pelletization of algae-fungi co-cultivation has never been achieved prior to the present invention.

Efficient production of biofuels from green algae would have significant implications in a wide range of industrial applications. However, the inability to effectively harvest such algae derived biofuels in a commercial setting has thus far limited its use. Therefore, a need exists for the development of a culturing system and method which provides for a more simplified harvest and increased yields. The present invention addresses this unmet need in the art.

SUMMARY OF THE INVENTION

A system for the production of a biological product is described. The system includes at least one fungus, at least one algae, and a growth medium, wherein the at least one fungus and at least one algae are co-cultivated in or on the growth medium to form a pellet containing the biological product.

In one embodiment, the at least one fungus is from a genus selected from the group consisting of Arthoniomycetes, Agaricomycetes, Basidiomycetes, Blastocladiomycetes, Chytridiomycetes, Dacryniycetes, Dothideomycetes, Geoglossomycetes, Glomeromycetes, Eurotiomycetes, Lecanoromycetes, Leotiomycetes, Lichinomycetes, Monoblepharidomycetes, Orbiliomycetes, Sordariomycetes, Tremellomycetes, Pezizomycetes, Zygomycetes, Mortierellales, Mucorales and combinations thereof.

In a further embodiment, the at least one algae is from a class selected from the group consisting of Actinochrysophyceae, Bacillariophyceae, Bryopsidophyceae, Bolidophyceae, Chlorarachnea, Chlorophyceae, Chrysophyceae, Cryptophyceae, Cyanophyceae, Diatomophyceae, Dinophyceae, Eustigmatophyceae, Glaucophyceae, Haptophyceae, Noctiluciphyceae, Pedinophyceae, Picophagophyceae, Pleurastrophyceae, Prasinophyceae, Prymnesiophyceae, Raphidophyceae, Synchromophycea, Syndiniophyceae, Synurophyceae, Trebouxiophyceae, Ulvophyceae, Xanthophyceae, and combinations thereof.

In another embodiment, the at least one algae is from a genus selected from the group consisting of *Actinocyclus, Bellerochea, Cyclotella, Cryptomonas, Monochrysis Chlorella, Chaetoceros, Dunalliela, Haematococcu, Nannochloropsis, Pleurochrysis, Gracilaria, Sargassum, Dunaliella, Cyclotella, Navicula, Nitzschia, Spirulina, Phaeodactylum, Thalassiosira, Skeletonema, Porphyra* and combinations thereof.

In another embodiment, the biological product is selected from the group consisting of a biofuel, a biomass, a terpenoid compound, a bioplastic, a pigment, an antioxidant, a vitamin, an antibiotic surfactant protein, a peptide, a lipid, a therapeutic compound and combinations thereof.

In another embodiment, the terpenoid compound is selected from the group consisting of squalene, limonene, botryococcene and combinations thereof.

In another embodiment, the therapeutic compound is a neutriceutical.

In another embodiment, the nutriceutical is an unsaturated fatty acid including DHA and EPA.

In another embodiment, the therapeutic compound is a protein, peptide or lipid.

In another embodiment, the ratio of fungus to algae is about 1 to 1.

In another embodiment, the ratio of fungus to algae is about 2 to 1.

In another embodiment, the ratio of fungus to algae is about 1 to 2.

In another embodiment, the growth medium is selected from the group consisting of waste water, lignocellulosic biomass, corn, waste from bioethanol, biofuel production, waste from industrial processes and combinations thereof.

In another embodiment, the pellet has a diameter ranging between 0.2-15 mm.

A method of producing a biological product is also described. The method includes the steps of co-cultivating at least one fungus with at least one algae in or on a growth medium, wherein the co-cultivated fungus and algae form a pellet from which the biological product is extractable.

In one embodiment, the biological product is selected from the group consisting of a biofuel, a biomass, a terpenoid compound, a bioplastic, a pigment, an antioxidant, a vitamin, an antibiotic surfactant protein, a peptide, a lipid, a therapeutic compound and combinations thereof.

In a further embodiment, the ratio of fungus to algae is about 1 to 1.

In another embodiment, the ratio of fungus to algae is about 2 to 1.

In another embodiment, the ratio of fungus to algae is about 1 to 2.

In another embodiment, the fungus and algae are co-cultivated for about 1 or more days.

BRIEF DESCRIPTION OF THE DRAWINGS

For the purpose of illustrating the invention, there are shown in the drawings various embodiments of the present invention. It should be understood, however, that the invention is not limited to the precise arrangements and/or instrumentalities of the embodiments shown in the drawings.

FIG. 1, comprising FIGS. 1A-1F, depicts an image analysis of co-cultivation pellets. FIG. 1A depicts a pure culture of the fungi *C. Echinulata* in liquid medium. FIG. 1B depicts the green algae *C. Vulgaris* in the medium being totally absorbed by the fungi pellet after 2-days co-cultivation. The pellet turned to green, and the medium became clear. FIG. 1C depicts confocal imaging of co-cultivation pellet composed of fungi hyphe and algae, where the algae are imbedded with the fungi hyphe as co-cultivation. FIGS. 1D, 1E and 1F depict Nile red staining of the co-cultivation pellet under confocal microscope, where the lipid accumulating algae and fungi are together in the co-cultivated pellets.

FIG. 2, comprising FIGS. 2A-2D, depicts biomass and lipid yield comparisons as well as the lipid profile comparisons of the co-cultivation and traditional cultivation of individual species (referred hereby as mono-cultivation). FIG. 2C also depicts that one category of major products are unsaturated fatty acids including, DHA and EPA.

FIG. 3, comprising FIGS. 3A and 3B, depicts pellets of co-cultivation *C. echinulata* and *C. Vulgaris* under different growth medium conditions. FIG. 3A depicts long term co-cultivation of fungi and algae in sugar-basic medium for three months. FIG. 3B depicts co-cultivation of fungi and algae in sugar-free medium for three days.

FIG. 4, comprising FIGS. 4A-4D, depicts characterization changes of the medium in the co-cultivation system. FIG. 4A depicts the cell number change of *C. Vulgaris* over time for different mix ratios of fungi and algae. FIG. 4B depicts cellulase activity in the different co-cultivation medium. FIG. 4C depicts a reduced sugar change in different cultural medium (■ mono-cultivation of *C. echinulata*; ▲ mono-cultivation of *C. Vulgaris*; ▼ co-cultivation of *C. echinulata* and *C. Vulgaris* at a ratio of 2:1; ♦ co-cultivation of *C. echinulata* and *C. Vulgaris* at a ratio of 1:1; ● co-cultivation of *C. echinulata* and *C. Vulgaris* at a ratio of 1:2). FIG. 4D depicts a pH change in the different cultural medium (■ mono-cultivation of *C. echinulata*; ▲ mono-cultivation of *C. Vulgaris*; ▼ co-cultivation of *C. echinulata* and *C. Vulgaris* at a ratio of 2:1; ♦ co-cultivation of *C. echinulata* and *C. Vulgaris* at a ratio of 1:1; ● co-cultivation of *C. echinulata* and *C. Vulgaris* at a ratio of 1:2).

FIG. 5, comprising FIGS. 5A-5C, depicts the biomass changes in the co-cultivation system compared to a mono-cultivation system during a three day period of time. FIG. 5A depicts co-cultivation of *C. echinulata* and *C. Vulgaris* at a ratio of 2:1. FIG. 5B depicts co-cultivation of *C. echinulata* and *C. Vulgaris* at a ratio of 1:1. FIG. 5C depicts co-cultivation of *C. echinulata* and *C. Vulgaris* at a ratio of 1:2.

FIG. 6, comprising FIGS. 6A-6C, depicts the lipid change in the co-cultivation system compared to a mono-cultivation system during a three day period of time. FIG. 6A depicts co-cultivation of *C. echinulata* and *C. Vulgaris* at a ratio of 2:1. FIG. 6B depicts co-cultivation of *C. echinulata* and *C. Vulgaris* at a ratio of 1:1. FIG. 6C depicts co-cultivation of *C. echinulata* and *C. Vulgaris* at a ratio of 1:2.

DETAILED DESCRIPTION

The present invention relates generally to a novel strategy to reduce the harvesting cost and increase the production yield for algae biofuel, nutriceuticals, therapeutics, and bioproducts through exploiting the pelletization feature of filamentous fungi fermentation. More particularly, the co-cultivation system and method of the present invention provides for the improved harvest of SCO microalgae, increased biomass, nutriceuticals, and lipid or hydrocarbon yields.

The present invention includes the co-cultivation of selected algae with selected fungi to produce pellets that effectively removes the algae from a liquid growth medium via the co-cultivation process. This pellitization system of the present invention also provides for the harvesting of material through standard filtration methods. The pelletization system of the present invention also enables simplified extraction methods. The co-cultivation system provides for the increase of biomass, nutriceuticals, bioproducts, and lipid production as compared to separate cultivation techniques.

The approach represents a straightforward yet powerful solution to enable economically viable algae biofuel production. The approach also has the potential to reduce the cost for a variety of algae bioproducts, therapeutics, and nutriceuticals. The present invention dramatically decreases lipid, unsaturated fatty acid, biomass and other bioproduct production costs for microalgae and can assist in the production of an economically viable third generation biofuel as well as a broad range of bioproducts. The approach also enables the integration of waste water treatment using fungi with algae biofuel and bioproduction. In the same way, the approach enables the integration of biomass conversion waste product utilization by fungi and $CO_2$ utilization by algae. The end result is that the approach will provide an enablement for the connection of second generation biofuel (lignocellulosic biomass-based advanced biofuel) and third generation biofuel and bioproduct (algae-based). For example, co-cultivation enables the effective and low cost separation of algae from liquid medium using filtration. The co-cultivation platform also readily integrates with both photobioreactor and a raceway growth system with only minor adjustment. Additionally, the combination of different types of algae and fungi provides for a diverse range of products including pigments, unsaturated fatty acids, antioxidants, biomass and other nutriceulticals/therapeutics not attainable by isolated monocultures. The system of the present invention can also be used to integrate microalgae biofuel production with waste water treatment, environmental remediation, biomass-based advanced biofuel production, and other commercial applications.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, "biofuels" refers to any fuel, fuel additive, aromatic compound, aliphatic compound, lipid and/or oil derived from a microorganism, including a biomass starting material such as algae.

As used herein, the term "hydrocarbon" generally refers to a chemical compound that consists of the elements carbon (C) and hydrogen (H). All hydrocarbons consist of a carbon backbone and atoms of hydrogen attached to that backbone. Hydrocarbons are of prime economic importance because they encompass the constituents of the major fossil fuels (coal, petroleum, natural gas, etc.) and biofuels, as well as plastics, waxes, solvents and oils.

The term "algae" includes unicellular or multicellular organisms formerly classified as plants, occurring in fresh or salt water or moist ground, that have chlorophyll and other pigments but lack true stems, roots, and leaves.

The term "fungus" or "fungi" includes a wide variety of nucleated, spore-bearing organisms that are devoid of chlorophyll. Examples of fungi include yeasts, molds, mildews, rusts, and mushrooms.

The term "bacteria" includes any prokaryotic organism that does not have a distinct nucleus.

The term "isolated" means altered or removed from the natural state or biological niche through the actions of a human being.

The term "antibiotic" includes any substance that is able to kill or inhibit a microorganism. Antibiotics may be produced by a microorganism or by a synthetic process or semisynthetic process.

The term "biofuel" means any type of fuel whose energy is derived from a biological carbon source, including lipids or hydrocarbon by-products from a microorganism, or from general biomass conversion.

The term "culturing" refers to the propagation of organisms on or in solid or liquid media of various kinds.

The term "nutriceutical" refers to a chemical that can serve for nutrition or pharmaceutical purposes.

The term "bioproduct" refers to any product that is from a biological source.

A "culture system" refers broadly to any system useful for culturing an organism. These can be ponds, raceways, bioreactors, plastic bags, tubes, fermenters, shake flasks, air lift columns, and the like.

The term "oil" refers to oil that is suitable in the production of biofuels. Such oil may or may not be completely free of co-extractants from the organism.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no deleterious effect on the composition.

The term "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the target infection or disease states.

The term "mutant" refers to a variant of a parental strain as well as methods for obtaining a mutant or variant in which the desired biological activity is similar to that expressed by the parental strain. The "parent strain" is defined herein as the original microorganism (e.g. *Chlorella*) strains before mutagenesis. Mutants occur in nature without the intervention of man. They also are obtainable by treatment with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means. They also are obtainable by introducing exogenous genes from another species. The strategy can be used to enable the organism to produce new products.

The term "variant" refers to a strain having all the identifying characteristics of the strains of algae or fungus and can be identified as having a genome that hybridizes under conditions of high stringency to the genome of the organism. A variant may also be defined as a strain having a genomic sequence that is greater than 85%, more preferably greater than 90% or more preferably greater than 95% sequence identity to the genome of the organism. A polynucleotide or polynucleotide region (or a polypeptide or polypeptide region) has a certain percentage (for example, 80%, 85%, 90%, or 95%) of "sequence identity" to another sequence, which means that, when aligned, that percentage of bases (or amino acids) are the same in comparing the two sequences. This alignment and the percent homology or sequence identity can be determined using publicly available software programs known in the art.

As used herein, an "instructional material" includes a publication, a recording, a diagram, or any other medium of expression which can be used to communicate the usefulness of the invention in the kit for the co-cultivation of algae and fungi as recited herein. Optionally, or alternately, the instructional material can describe one or more methods of co-cultivating algae and fungi. The instructional material of the kit of the invention can, for example, be affixed to a container which contains one or more components of the invention or be shipped together with a container which contains one or more components of the invention. Alternatively, the instructional material can be shipped separately from the container with the intention that the instructional material and the various components be used cooperatively by the recipient.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Further, all numerical designations, e.g., pH, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

Algae Suitable for Increased Lipid, Nutriceutical, Biomass, Proteins, and Bioproduct Production The present invention relates to the cultivation of algae for producing lipids and biomass for the production of biofuels as well as nutriceuticals, therapeutics, and other bioproducts for pharmaceutical and other applications. These algae can be co-cultivated with filamentous fungi, as described hereinthroughout, to improve production yields of biomass, lipid, nutriceuticals, and other bioproducts, while decreasing overall harvesting costs.

As contemplated herein, any algal species may be used with acceptable results. Exemplary algae species include, without limitation, those from the classes Actinochrysophyceae, Bacillariophyceae, Bryopsidophyceae, Bolidophyceae, Chlorarachnea, Chlorophyceae, Chrysophyceae, Cryptophyceae, Cyanophyceae, Diatomophyceae, Dinophyceae, Eustigmatophyceae, Glaucophyceae, Haptophyceae, Noctiluciphyceae, Pedinophyceae, Picophagophyceae, Pleurastrophyceae, Prasinophyceae, Prymnesiophyceae, Raphidophyceae, Synchromophyceae, Syndiniophyceae, Synurophyceae, Trebouxiophyceae, Ulvophyceae, Xanthophyceae, or the genus *Actinocyclus, Bellerochea, Cyclotella, Cryptomonas, Monochrysis Chlorella, Chaetoceros, Dunalliela, Haematococcu, Nannochloropsis, Pleurochrysis, Gracilaria, Sargassum, Cyclotella, Navicula, Nitzschia, Spirulina, Phaeodactylum, Thalassiosira, Skeletonema,* and *Porphyra*. For example, in one embodiment, *Chlorella vulgaris*, which is single-celled green algae, can be used in the systems and methods of the present invention. *Chlorella vulgaris* is one of the most commonly used algae species for lipid and protein production due to its relatively high lipid content and strong resistance to contamination. In other exemplary embodiments, other *Chlorella* species such as *Chlorella minustissima, Chlorella pyrenoidosa*, and *Chlorella variabilis* can be used. It should be appreciated that any species of any class or genus identified herein may be used in the system and methods of the present invention, as described hereinthroughout. In still other embodiments, combinations of two or more algae may be used, or a mutant or engineered algae, as described in greater detail below, may be used.

Fungi Suitable for Co-Cultivation

Filamentous fungi have been broadly used for the industrial production of various proteins, lipids and other therapeutics. For example, filamentous fungi like *Mortierella isabellina, Mucor circinelloides* and *Cunninghamella echimdata* have been used for lipid production.

In one aspect, the present invention includes the cultivation of fungi capable of producing lipids, proteins, unsaturated fatty acids, polysaccharides, and other bioproducts. In another aspect, the present invention includes the cultivation of fungi capable of adopting the pellet morphology during cultivation.

In one embodiment of the present invention, any one of the fungi species described herein can be co-cultivated along with any of the algae species described herein for the efficient harvest of biofuels, unsaturated fatty acids, antioxidants, proteins, nutriceuticals, and any other bio or chemical products. Exemplary fungi species may include, but are not limited to, the class Arthoniomycetes, Agaricomycetes, Basidiomycetes, Blastocladiomycetes, Chytridiomycetes, Daerymycetes, Dothideomycetes, Geoglossomycetes, Glomeromycetes, Eurotiomycetes, Lecanoromycetes, Leotiomycetes, Lichinomycetes, Monoblepharidomycetes, Orbiliomycetes, Sordariomycetes, Tremellomycetes, Pezizomycetes, Zygomycetes, or the orders Mortierellales, Mucorales, and such. In one exemplary embodiment, *C. echinulata* demonstrates strong adsorption capacity for various biomolecules including metal, ions, and others, which also allows the species to be widely used for waste water treatment. In still other embodiments, combinations of two or more fungi may be used, or a mutant or engineered fungi, as described in greater detail below, may be used.

As contemplated herein, the present invention also includes fungi (or algae), wherein the fungi or algae strain was serially propagated. When strains are serially propagated, some of the characteristics of the strain may change. Such changes include deletion or suppression of metabolic pathways, an increase in certain metabolic pathways, changes to the chromosome, genes and/or operons (e.g. via mutations or changes in the regulatory factors that control the expression level of said genes or operons). Such changes to the metabolic characteristics and/or genetic make-up may increase and/or decrease the production of biofuel, therapeutics, proteins, bioplastics, surfactant, vitamins, antibiotics, terpenoids like botryococcene, limonene, and squalene, and many other bioproducts. Methods for isolating mutant cells with a desired characteristic are well known in the art, See, for example, U.S. Pat. No. 5,348,872, which is herein incorporated by reference in its entirety.

Co-Cultivation of Algae and Fungi

Co-cultivation of fungi and algae can be difficult due to differences in optimal conditions between species. The controlled co-cultivation for pelletization is achieved through multiple microalgae and fungi strain screening for co-cultivation compatibility as well as for cultivation condition optimization. It should be appreciated that any substrates suitable for promoting fungal growth or alternatively algae growth may be used in the co-cultivation platform, as described in more detail below, and as would be understood by those skilled in the art.

Co-cultivation may include the step of pre-culturing either or both of the algae and fungi species prior to co-cultivation, where each pre-culturing step may be for a variable period of time. For example, in one embodiment of the present invention, the algae species can first be pre-cultured prior to co-cultivation. In another embodiment of the present invention, the fungi species can be pre-cultured prior to co-cultivation. In still other embodiments, both the algae and fungi are pre-cultured. Of course, neither the algae nor the fungi are required to be pre-cultured, as preculturing is an optional step.

In another embodiment of the present invention, spores of the fungi species can be directly supplanted into algae growth medium.

After pre-culturing (if any), the combination of algae and fungi species into a co-cultivation platform may occur with different relative amounts of each species. While three examples have been described herein at particular ratios, the actual ratio can be much more flexible. Thus, in certain embodiments of the present invention, the ratio of algae to fungi species within the co-cultivation platform can vary. For example, in one embodiment, the ratio of algae to fungi is about 1 to 1. In another embodiment, the ratio of algae to fungi is about 1.5 to 1. In another embodiment, the ratio of algae to fungi is about 2 to 1. In another embodiment, the ratio of algae to fungi is about 2.5 to 1. In another embodiment, the ratio of algae to fungi is about 3 to 1, In another embodiment, the ratio of algae to fungi is about 1 to 1.5. In another embodiment, the ratio of algae to fungi is about 1 to 2. In another embodiment, the ratio of algae to fungi is about 1 to 2.5. In another embodiment, the ratio of algae to fungi is about 1 to 3. In another embodiment, the amount of algae is between 1 and 500% more than the amount of fungi. In another embodiment, the amount of fungi is between 1 and 500% more than the amount of algae.

As explained hereinthroughout, pelletization of fungal species has been shown to lead to increased lipid production during fungal cultivation. Formation of pellets also allows for easier harvest of produced lipids through simple filtration and extraction. One aspect of the present invention includes the use of fungal pelletization to capture algae and algae sourced lipids, biomass, proteins, and various bioproducts. In certain embodiments of the present invention, pellets may have a diameter of greater than 1 mm, greater than 2 mm, greater than 3 mm, greater than 4 min or greater than 5 mm. In other embodiments, the pellets may have diameters ranging between 0.2-15 mm. In a preferred embodiment, the pellets may have diameters ranging between 0.5-10 mm. In another preferred embodiment, the pellets may have diameters ranging between 1-3 mm. As contemplated herein, there is no limitation of the present invention based on specific or average pellet size.

In certain embodiments of the present invention, pelletization (and thus removal of algae from media) can occur within a variable co-cultivation time period. For example, pelletization and substantial removal of algae from the growth media can occur within about 1 day of co-cultivation. In another embodiment, pelletization and substantial removal of algae from the growth media can occur within about 1.5 days of co-cultivation. In another embodiment, pelletization and substantial removal of algae from the growth media can occur within about 2 days of co-cultivation. In another embodiment, pelletization and substantial removal of algae from the growth media can occur within about 3 days of co-cultivation. In another enablement, pelletization can occur over a week, several weeks, a month, several months, or over a year of cultivation. For example, pelletization can occur during three months of cultivation. As used herein, "substantial removal of algae" from the growth media may mean more than 50% removal, more than 60% removal, more than 70% removal, more than 80% removal, more than 90% removal, more than 95% removal, more than 96% removal, more than 97% removal, more than 98% removal, or more than 99% removal. It should be appreciated that the co-cultivation time necessary for the substantial removal of algae from the growth media will vary based on the fungi and/or algae selected, the ratio of fungi to algae, and the composition of the growth media. Furthermore, any one of these features may be adjusted to control the pelletization and harvesting process.

Growth Substrates and Co-Culturing of Fungi and Algae

It should be appreciated that any substrate suitable for promoting fungal and algal growth may be used, in any ratios and combinations, as would be understood by those skilled in the art. In certain embodiments, high starch substrates may promote optimal co-cultivation. In certain embodiments, only $CO_2$ is needed as a carbon source. The utilization of $CO_2$ only will provide a platform for complete autotrophic biofuel and bioproduct production. Given that $CO_2$ is a waste product for ethanol biofuel fermentation, the platform can harness the by-products or waste products from first or second generation biofuel (corn, sugarcane, and biomass-based) for third generation biofuel and bioproduct production (algae-based). In certain embodiments, cellulose may also be a suitable substrate for co-cultivation. Given the enormous volumes of accumulating cellulitic biomass and the utilization of foodstuff grains in alcohol (fuel) production, microorganisms that utilize cellulose are quite attractive.

For example, in some embodiments, the culture media for co-culturing may include substrates comprising oatmeal, barley, or potato agar bases. The culture media may also be a PDA medium, a cellulose medium, and may include starch, glucose, or any combination of standard components. Further, the selected fungal and algal strains may be grown in a medium containing any combination of inorganic salts, organic nitrogen sources, such as peptones, defatted cotton seed flour, corn steep liquor, or yeast extract and carbon source. Examples of a carbon source may include, but is not limited to, glucose, lactose, sucrose, cellulose or other carbohydrates. Sugar free, or reduced sugar substrates may also be used. For example, some fungi species may use sugars from the algae cell wall to feed fungal growth, thereby allowing for grown under sugar-free conditions. Further still, it should be appreciated that the present invention should not be limited by the type or amount of growth media used, and should include use of any media suitable for cultivating fungi and/or algae as would be understood by those skilled in the art. In other embodiments, these conditions can also include culturing microorganisms in the absence of oxygen (anaerobic conditions) or in reduced oxygen conditions (e.g., microaerophilic conditions).

Generally speaking, the co-cultures can be cultured on a large scale for commercial use, by using conventional fermentation techniques. In this context fermentation is used broadly to refer to any controlled fungal/algal culturing conditions. Prior to large scale growth an inoculum of said growth culture is generally cultured. In certain embodiments, the fungi and algae can be co-cultured in a bioreactor vessel for a scaled up production of lipid and/or biomass in general. For example, photobioreactors and raceway culture systems may be used. As contemplated herein, any conventional bioreactor vessel can be used as the vessel for the purpose of this invention. For example, the vessel may be made of materials such as stainless steel, glass, plastic, and/or ceramics, and may have a volume of from about 100 ml to 50,000 L or larger. The bioreactor vessel may be connected to a series of storage flasks that contain nutrient solutions and solutions for maintaining and controlling various parameters of the co-cultivation and biomass/lipid recovery process. Depending on the particular needs of the fermentation, there may be separate storage flasks for individual supply of substrates to the vessel, which substrates serve as the carbon, nitrogen or mineral source for the living cells in the vessel.

Further, several methods can be used to grow the various microorganisms for use in the invention. Fed Batch culture is a variation on ordinary batch culture and involves the addition of a nutrient feed to the batch. Cells are cultured in a medium in a fixed volume. Before the maximum cell concentration is reached, specific supplementary nutrients are added to the culture. The volume of the feed is minimal compared to the volume of the culture. Fed batch culture typically proceeds in a substantially fixed volume, for a fixed duration, and with a single harvest either when the cells have died or at an earlier, predetermined point.

In a continuous culture, the cells are initially grown in a fixed volume of medium. To avoid the onset of the decline phase, fresh medium is pumped into the bioreactor before maximum cell concentration is reached. The spent media, containing a proportion of the cells, is continuously removed from the bioreactor to maintain a constant volume. The process also removes the desired product, which can be continuously harvested, and provides a continuous supply of nutrients, which allows the cells to be maintained in an exponentially growing state. Theoretically, the process can be operated indefinitely. Continuous culture is characterized by a continuous increase in culture volume, an increase and dilution of the desired product, and continuous maintenance of an exponentially growing culture.

Perfusion culture is similar to continuous culture except that, when the medium is pumped out of the reactor, cells are not removed. As with a continuous culture, perfusion culture is an increasing-volume system with continuous harvest that theoretically can continue indefinitely.

Mutant or Engineered Microorganisms for Enhanced Production of Co-Cultivation Pellets The present invention also includes mutant or engineered fungi and/or algae that ultimately increase the production yield of at least one of biomass and lipids, or the speed at which the mutant or engineered fungi and/or algae can produce at least one of biomass and lipids. Mutant or engineered fungi and/or algae can also empower the system to produce the broader range of bioproducts including terpenoid, surfactant, therapeutics, nutriceuticals, pigments and others. Mutant or engineered fungi and/or algae are obtainable by treatment of the microorganism with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

For example, the present invention also includes identifying and cloning genes that encode for the production of lipids by any microorganism described herein. Thus, the present invention encompasses an isolated nucleic acid molecule from a microorganism encoding a polypeptide involved in the synthesis or production of a lipid. In another embodiment, an isolated nucleic acid molecule is at least 65%, at least 70%, at least 75%, at least 80%, at least 85%, at least 90%, at least 95%, at least 96%, at least 97%, at least 98%, or at least 99% identical to said isolated nucleic acid molecule from any one of the microorganisms described herein. In another embodiment, a polypeptide sequence is at least 65%, at least 70%, at least 75%, at least 80%, at least 85%, at least 90%, at least 95%, at least 96%, at least 97%, at least 98%, or at least 99% identical to a polypeptide from any one of the microorganisms described herein.

Methods to clone and/or probe genomes for synthetic pathways may include creating cDNA and/or genomic libraries, and screening the libraries for genes that produce lipids. Thus, the present invention comprises a DNA and/or chromosomal library of any one of the microorganisms described herein. In one embodiment, the library is cloned into a vector that can replicate in a prokaryotic cell and/or eukaryotic cell. In another embodiment, the eukaryotic cell is a fungal cell. In another embodiment, the library is a lambda phage, Yeast Artificial Chromosome, Bacterial Artificial Chromosome, and/or cDNA. In another embodiment, the library is screened for production of at least one lipid.

Another method for determining the gene, genes and/or operon(s) that encode for the production of lipids include mutagenizing the genome of any one of the microorganisms described herein and looking for an increase, addition, reduction or removal of a lipid. This can be accomplished via chemical and/or transposon mutagenesis. Once a gene, genes and/or operon(s) is identified, said gene, genes or operon(s) can be cloned and/or isolated. Thus, one embodiment of the invention comprises an isolated nucleic acid of any one of the microorganisms described herein, wherein the nucleic acid molecule is cloned into a vector. In another embodiment, said nucleic acid molecule encodes for a gene, genes, or operon(s) that encode for proteins involved in the production of lipids. In another embodiment, the vector autonomously replicates or integrates into the host's chromosome. In another embodiment, said vector is transformed or transfected into a heterologous cell. In another embodiment, said heterologous cell is selected from the group consisting of a prokaryotic or eukaryotic cell.

The present invention also encompasses variants and fragments of polynucleotides and/or proteins of any one of the microorganisms described herein that produce or are part of the pathway(s) that produce lipids. The variants may contain alterations in the nucleotide and/or amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both. In addition, the nucleotides can be sequenced to ensure that the correct coding regions were cloned and do not contain any unwanted mutations.

Nucleic acid molecules encoding one or more biosynthetic enzyme or protein, and orthologs and homologs of these sequences, may be incorporated into transformation or expression vectors of any one of the microorganisms described herein. As used herein, the term "vector" refers generally to a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Once the gene(s) and/or operon(s) of any one of the microorganisms described herein have been identified, cloned, transformed, transfected or infected into a heterologous organism (or new organism from a synthetic genome), the heterologous organism can be grown to produce and purify the desired lipids.

Thus, the present invention also includes a method for generating mutant strains of a microorganism with an increased production rate or production amount of at least one lipid. The method includes the steps of mutating the microorganism, culturing the mutated microorganism, and screening the cultures of mutated microorganism for enhanced production rate or production amount of at least one lipid.

As contemplated herein, the same molecular techniques as described for mutating or engineering a microorganism for the enhanced production of a lipid may also be used for increasing the growth rate and/or the size of the microorganism for increased yields of biomass, surfactant like squalene, synthetic hydrocarbon fuel like limonene, therapeutic proteins like insulin, nutriceuticals like DHA, and other bioproducts like bioplastics, as would be understood by those skilled in the art.

Increase of Lipids, Hydrocarbons, Nutriceuticals, Therapeutics, Bioproducts, and Biomass Produced by Fungi-Algae Co-Cultivation As stated previously, the present invention relates in part to the co-cultivation of fungi and algae for the efficient production and capture of lipids. It should be appreciated that identities of produced lipids may depend upon the particular species of algae and/or fungi that is selected for co-cultivation, and therefore, the present invention may be used for the production of any lipid, hydrocarbon, or for the general production of biomass.

In certain embodiments, the extracted lipids or other by-products may be useful for the production of biofuels, plastics, therapeutics, plasticizers, nutriceuticals, vitamins, antibiotics, rubber, fuel additives, and/or adhesives. For example, extracted lipids may include unsaturated fatty acids useful for the production of nutraceuticals.

In other embodiments, the co-cultivation of selected algae and fungi species can be directed for the production and harvest of therapeutics, such as proteins, chemical species, short peptides, and other biomolecules.

It should also be appreciated that the co-cultivation provides for an increase in production of any of the aforementioned products described herein, including biomass, lipid, nutriceuticals, and other bioproducts. In certain embodiments, the biomass, lipid, nutriceuticals, and other bioproducts increase by at least 1.5 fold, at least 2 fold, at least 2.5 fold, at least 3 fold, at least 3.5 fold, at least 4 fold, at least 4.5 fold or at least 5 fold, as compared to monocultures. In certain embodiments, the biomass and total proteins increase between 1 and 10 to fold. In any case, the co-cultivation at least increases production of the desired product over that of any monoculture of the same algae or fungus.

Kits

The present invention also provides for a kit comprising one or more containers filled with one or more of the ingredients and/or components of the invention. Thus, the present invention provides kits that can be used to perform any of the methods described herein. In one embodiment, a kit comprises at least one fungi strain, such as *Cunninghamella echinulata*, in one or more containers, and at least one algae strain, such as *Chlorella vulgaris*, in one or more containers. The organisms can be supplied frozen in media, freeze dried and/or as spores (if applicable). The kit may also include instructional material for growing the fungi and/or algae under optimal conditions for mono-cultivation, as well as for co-cultivation. The methods in the instructions may include specific bioreactor volumes, purification schemes, optimal temperatures, pH, and/or other conditions. The kit may also include a growth media for each microorganism if grown as a mono-cultivation, or as a co-cultivation. The media contained in the containers of these kits may be present as a ready-to-use formulation, or as a more concentrated formulation. In addition, the media can be supplied in dry powder. Thus, a kit can comprise a dry power of the media of the invention and a liquid to suspend the media. The liquid may be water or buffers known in the art. Filters for sterilization of the media may also be provided.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way any portion of the disclosure.

The co-cultivation of multiple species is challenging because the optimal cultivation conditions and growth rate for different species, especially for species from different phylum, are rather different. The controlled co-cultivation for pelletization was achieved through multiple microalgae and fungi strain screening for the co-cultivation compatibility as well as cultivation condition optimization. Two co-cultivation platforms are presented as examples of sugar-based and sugar-free platforms. The first platform involves co-cultivation of Chlorella vulgaris with oleaginous fungi Cunninghamella echinulata. The C. echinulata has been shown to have strong adsorption capacity for various biomolecules including metal, ions, and others, which allows the species to be widely used for waste water treatment (El-Morsy, 2005, Mycologia 97(1): 286-286). C. vulgaris is one of the most commonly used algae species for lipid and protein production due to its relatively high lipid content and strong resistance toward different contamination.

The following methods were used in the Examples of the present invention:

Microorganisms and Pre-Cultivation

Oleaginous fungi Cunninghamella echinulata (Strain ID: NRRL 3655) was obtained from the USDA-ARS (United States Department of Agriculture, Agriculture Research Service) Culture Collection (Peoria, USA). Green algae Chlorella Vulgaris UTEX 259 was obtained from the University of Texas Algae Collection. Pre-cultivation was carried out by standard techniques for each species to allow both microalgae and fungi to grow to a plateau phase to accumulate enough biomass.

C. vulagris was first cultivated in 50 mL TAP medium in 250 mL Erlenmeyer flasks at 25□ for 3 days. The TAP medium was composed of (g/L) Tris base, 2.42; $NH_4Cl$, 0.375; $MgSO_4.7H_2O$, 0.1; $CaCl_2.2H_2O$, 0.05; $K_2HPO_4$, 0.108; $KH_2PO_4$, 0.054; glacial acetic acid, 1 mL/L, and Hutner's trace elements, 1 mL/L. The Hutner's trace elements was composed of (g/L) EDTA disodium salt, 50; $ZnSO_4.7H_2O$, 22; $H_3BO_3$, 11.4; $MnCl_2.4H_2O$, 5.06; $CoCl.6H_2O$, 1.61; $CuSO_4.5H_2O$, 1.57; $(NH_4)_6Mo_7O_{24}.4H_2O$, 1.10; $FeSO_4.7H_2O$, 4.99; and KOH, 17. The culture was under constant light and shaking at 150 rpm for 7 days. The culture was then transferred to 1 L Erlenmeyer flasks with 400 mL TAP medium and incubated in the same condition for 84 hours which reached the cell density about $3 \times 10^8$ cell/mL. The culture was then ready for mixing with the pre-cultivated oleaginous fungi.

Fungal pre-cultivation was carried out in two approaches, heterotrophic cultivation and sugar-free cultivation. For heterotrophic pre-cultivation, a loop of fungal mycelia from a slant was incubated on PDA medium in 250 mL Erlenmeyer flasks at 28° C. to form spores. After five days of incubation, the spores were washed from the agar with sterile water and then transferred into 400 mL potato detrose broth (PDB, Difco 254920, Sparks, Md.) in 1 L Erlenmeyer flasks with the final spore concentration of about $3.44 \times 10^7$ spores/L.

The spore solution was then cultivated at 28° C. with a shaking speed of 150 rpm for 36 hours to achieve pelletization.

In order to evaluate a complete autotrophic platform, where fungus can grow on the algae cell wall carbohydrate, pre-cultivation in a sugar-free medium was performed. For sugar-free pre-cultivation, the spores were generated and collected in the same way described above in distilled water. Instead of PDB medium, the spores were first incubated in distilled water at room temperature for 6 hours, and then transferred to modified TAP medium for cultivation at 28° C. with a shaking speed of 150 rpm for 24 hours. The modified TAP medium was composed of additional 100 mL sodium acetate buffer (50 mM, pH 4.8) and 0.5 g $MgSO_4.7H_2O$, 0.1 in 1000 mL TAP medium.

Co-Cultivation

The pre-cultured Chlorella vulgaris and Cunninghamella echinulata were mixed at three different ratios: 2:1, 1:1 and 1:2 (algae to fungi) to reach a total volume of 90 mL in the 250 mL Erlenmeyer flasks. The mixed fungi and algae were then further cultivated at 25° C. under constant light. The co-cultivation systems were shaken at 120 rpm. Pure fungi and green algae samples were cultured at the same conditions for use as controls.

Biomass Assay

The co-cultivation biomass was harvested by centrifugation every day for three days (0, 1, 2 and 3 days). Harvested biomass was washed with the same volume of distilled water three times to remove residual nutrients, and then dried at 60° C. in weighed tubes for 3 days. The weight of biomass can be measured and recorded as grams of dry weight per liter of culture medium. For comparison, the independently cultivated fungi and green algae were mixed at the same three aforementioned ratios to serve as the controls for biomass analysis, and were harvested using the same methods.

Lipid Determination

Total lipid was extracted using the sulphuric acid-methanol method as previously described (O'Fallon, J V. et al., A direct method for fatty acid methyl ester synthesis: application to wet meat tissues, oils, and feedstuffs. J Anim Sci 85:1511-1521 (2007)). The method involves direct transesterification of total lipid into Fatty Acid Methyl Ester (FAME). The extracted FAME was collected in pre-weighed tubes and dried 3 days, and the tubes were then weighted to derive the total lipid yield. The lipid composition was analyzed by GC/MS using an Agilent 7890 GC (Agilent Technologies) coupled with an Agilent 5975 inert mass spectrometer. For GC/MS analysis, the HP-5MSI column was used. The temperature of injection was set at 280° C. and temperature of MS transfer line was 100° C. The GC oven temperature was programmed as follows: initial temperature 40° C. for 0.5 min, 40-110° C. at 5° C./min, and 110-300° C. at 20° C./min, and a total run time of 24 min. The raw chromatography and mass spectrum data were processed with Enhanced Chemstation (Agilent Technologies)

Nile Red Staining

The co-cultivated pellets were collected by centrifugation from 5 mL of culture, and then re-suspended in 5 mL of 25% DMSO. Previously described staining protocols were used (Chen, W. et al. Microwave-assisted Nile red method for in vivo quantification of neutral lipids in microalgae. Bioresour. Technol. 102: 135-141 (2011)) and also modified. Specifically, the pellets were mixed with 3 μl of Nile Red stock solution (0.15 mg/ml dissolved in acetone) and further incubated at 50° C. with shaking at 150 rpm for 5 min. The Nile Red stained pellets were then used for confocal microscopy analysis to observe lipid droplet formation in the co-cultivated cells.

Confocal Microscopy Analysis and Regular Microscopy Analysis

Confocal microscopy was used for observing lipid droplet accumulation as well as integration of algae and fungal cells. An Olympus FV1000 laser scaning confocal microscope equipped with a Coolsnap CF monochrome CCD camera (Photometrics, Tucson, Ariz.) controlled by MetaView version 5.2 software (Molecular Devices, Downingtown, Pa.) was used. Light microscopy was used to observe the co-cultivation morphology.

Sugar and Cellulose Assay

The co-cultivation supernatants were collected by centrifugation from the culture medium for the sugar and cellulase assays. The free reduce sugar was analyzed by the DNS (3, 5-dinitrosalicylic acid) reagent via absorbance at 540 nm with a glucose standard according to the modified method from Behera (Tolonen, A. C. et al, Proteome-wide systems analysis of a cellulosic biofuel-producing microbe. *Mol Syst Biol* 7:461 (2011)). Cellulase activities in the medium were tested in the term of "filter-paper-unite" (FPU) following the Laboratory Analytical Procedure (LAP 006) from the National Renewable Energy Laboratory (NREL) (Project, E. Procedure Title: LAP-006 Measurement of Cellulase Activities Date. *Chemical Analysis and Testing Task Laboratory Analytical Procedure* LAP006 7-18 (1996)).

Example 1: Pellitization Through Co-Cultivation

The present invention includes co-cultivation techniques for algal biofuel production. As contemplated herein, proper control of co-cultivation conditions allows for the formation of pellets containing both aglae and fungi that lead to an efficient harvest of algae from a growth medium.

Figure 1:
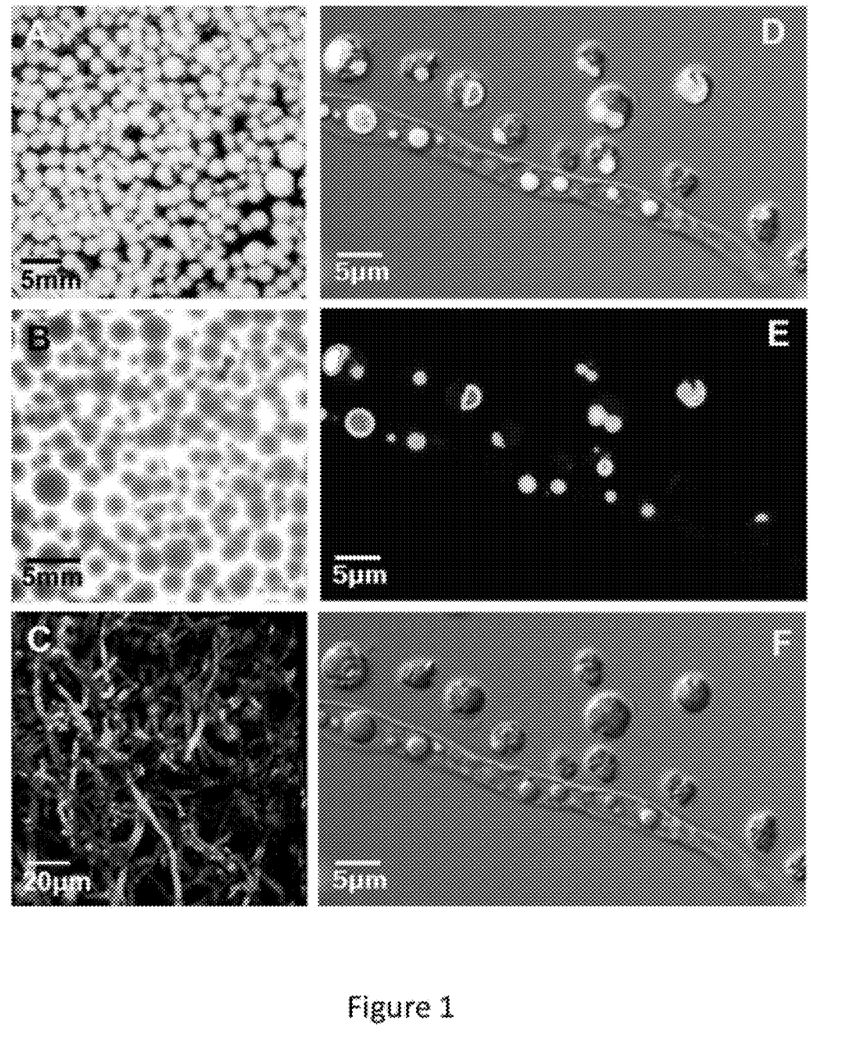
Figure 4:
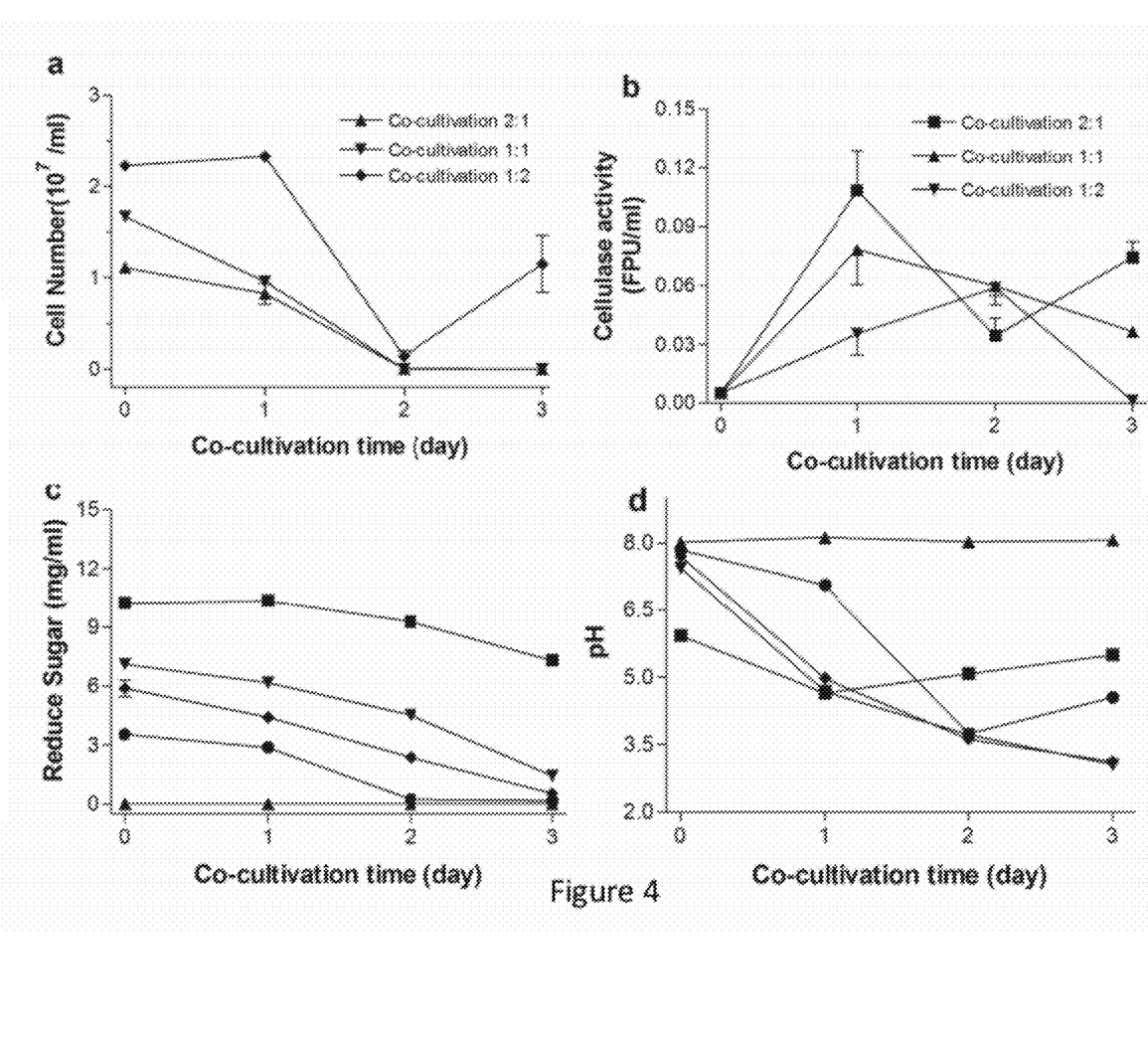

Various evaluations of the cultivation performance for co-cultivation were performed. As shown in FIG. 1B, the co-cultivation of *C. vulgaris* and *C. echintrata* formed pellets of about 1 mm to 3 mm in size pellets. As shown in FIG. 1C, composition analysis of the pellets by confocal microscope revealed that the algae cells are embedded in the fungal conidia. As contemplated and described hereinthroughout, pelletization can be achieved at various algae-fungi ratios. Additionally, and depending on growing conditions, complete harvest can be reached and subsequent removal of algae from the liquid medium after 2 days co-cultivation. As shown in FIG. 4A, even at a ratio of 1:2 combination of fungi and algae, nearly 99% removal of *C. vulgaris* from the liquid medium can be achieved on the second day after co-cultivation.

Figure 2A:
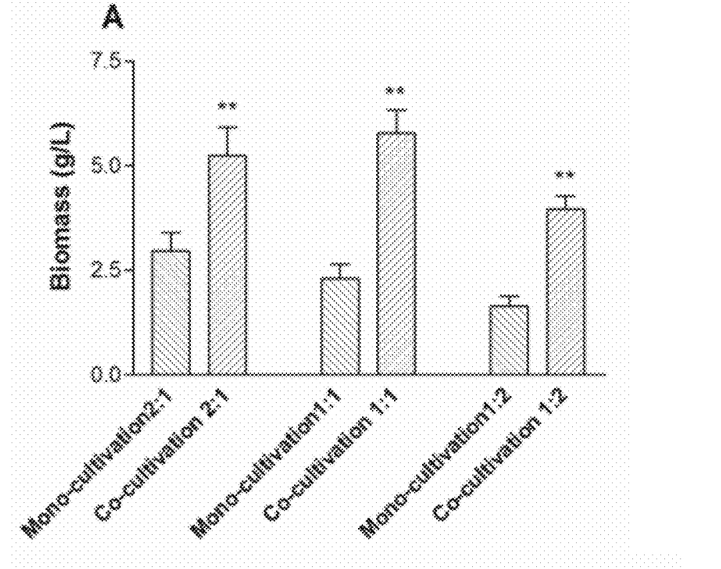
FIG. 2A depicts the biomass change of the co-cultivation system after two days co-cultivation of *C. echinulata* and *C. Vulgaris* at different ratios.
Figure 2B:
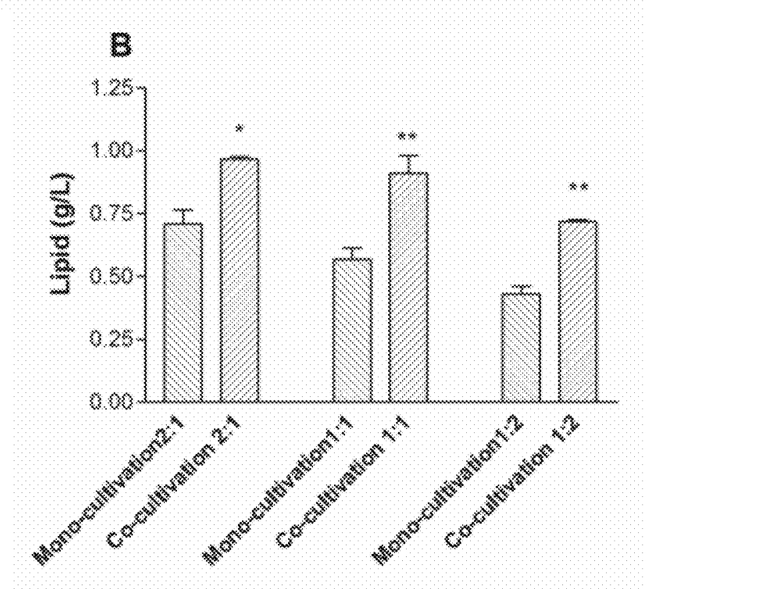
FIG. 2B depicts the lipid change of the co-cultivation system after two days co-cultivation of *C. echinulata* and *C. Vulgaris* at different ratios.
Figure 2C:
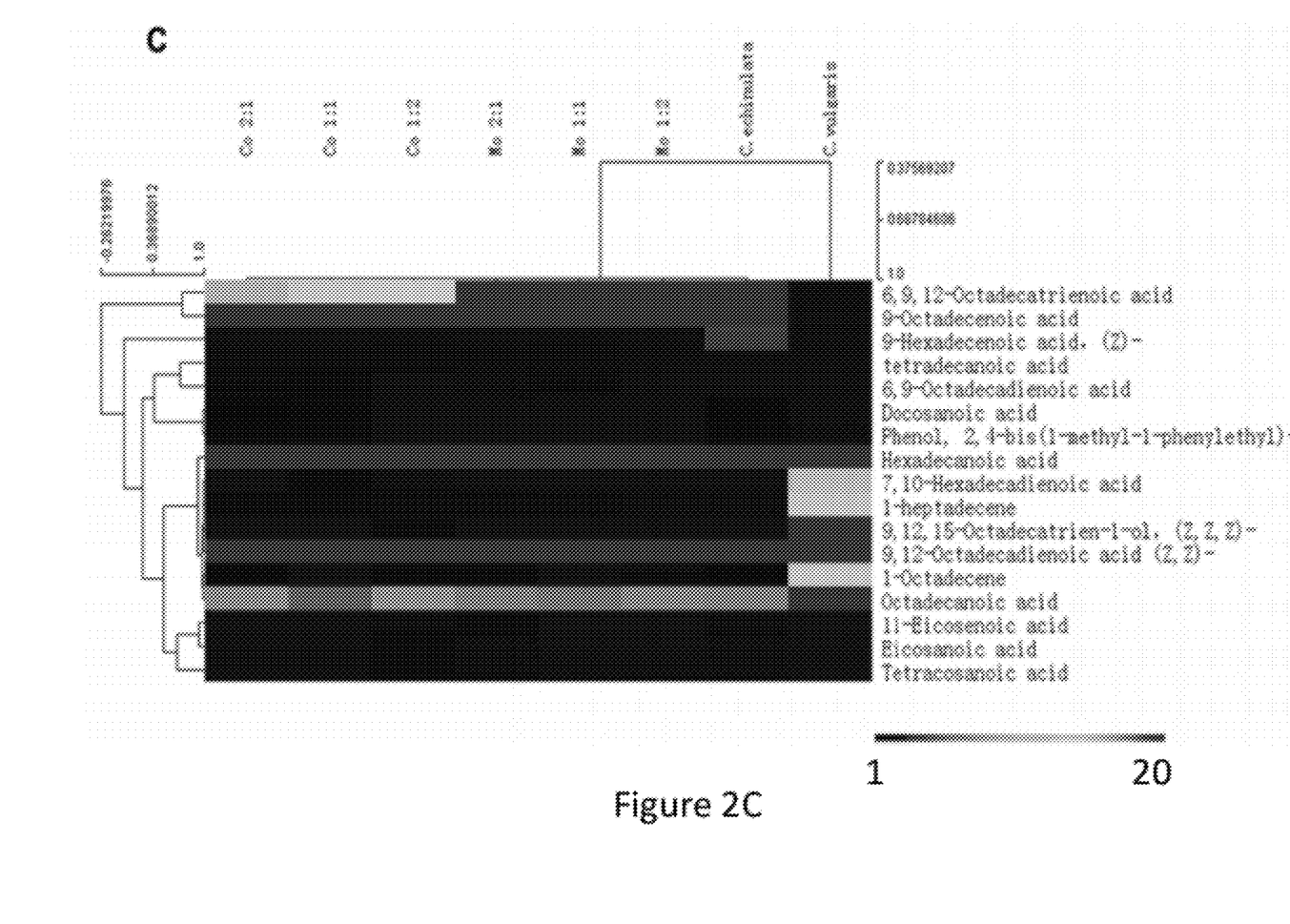
FIG. 2C depicts GC/MS analysis of co-cultivation lipid as compared to mono-cultivation lipid, which shows that the co-cultivation has similar lipid profile to the mixture of the two cultivations.
Figure 2D:
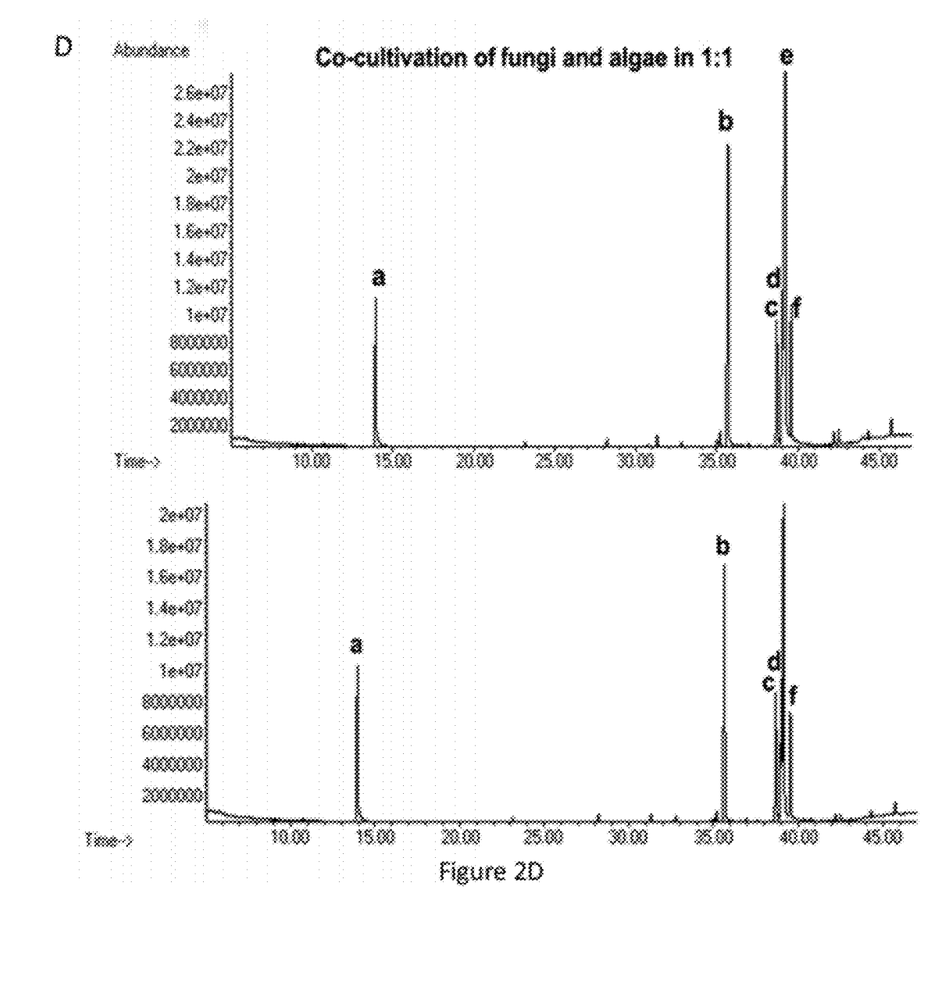
FIG. 2D is a GC chromatogram in support of FIG. 2C.
Figure 5:
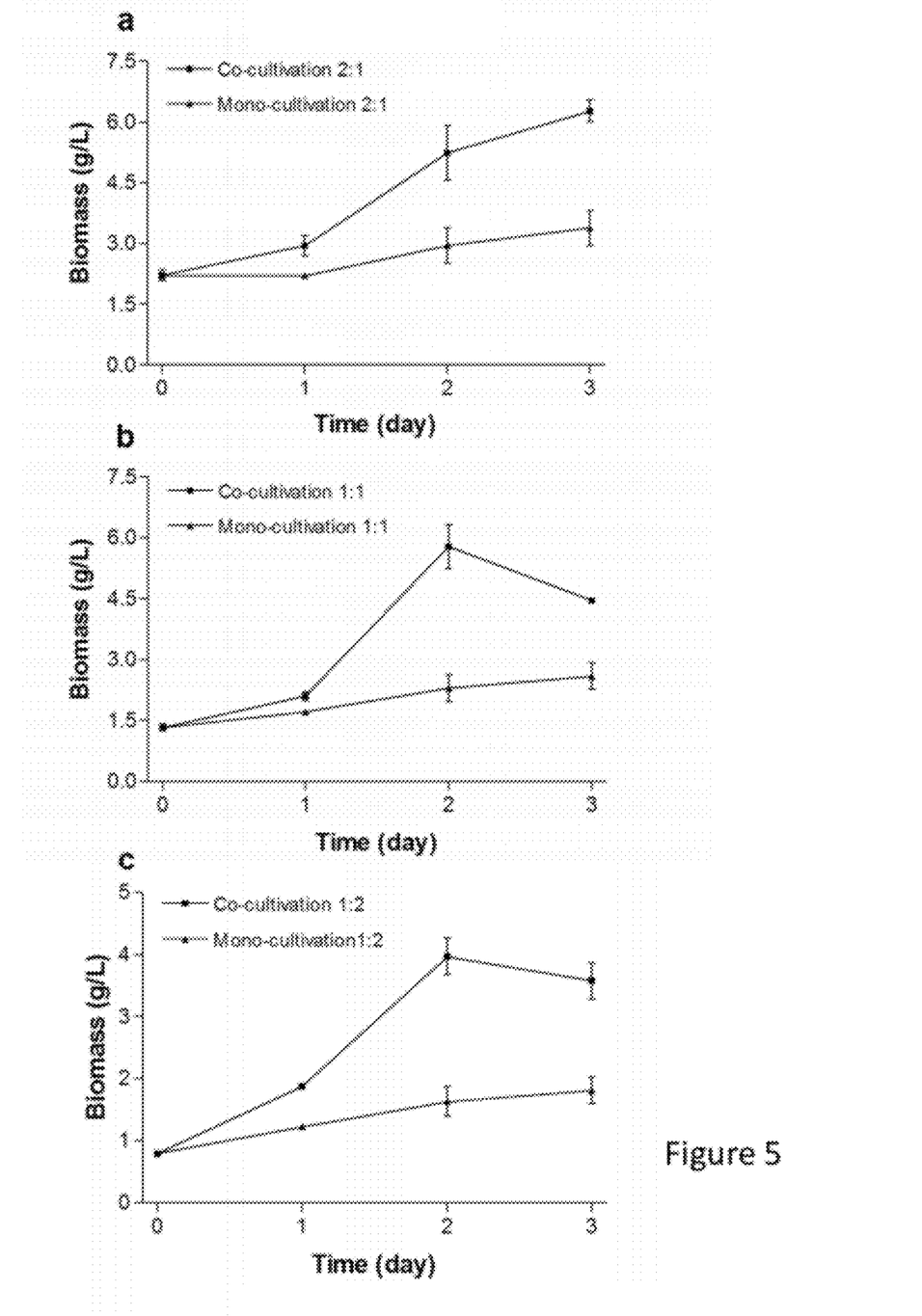
Figure 6:
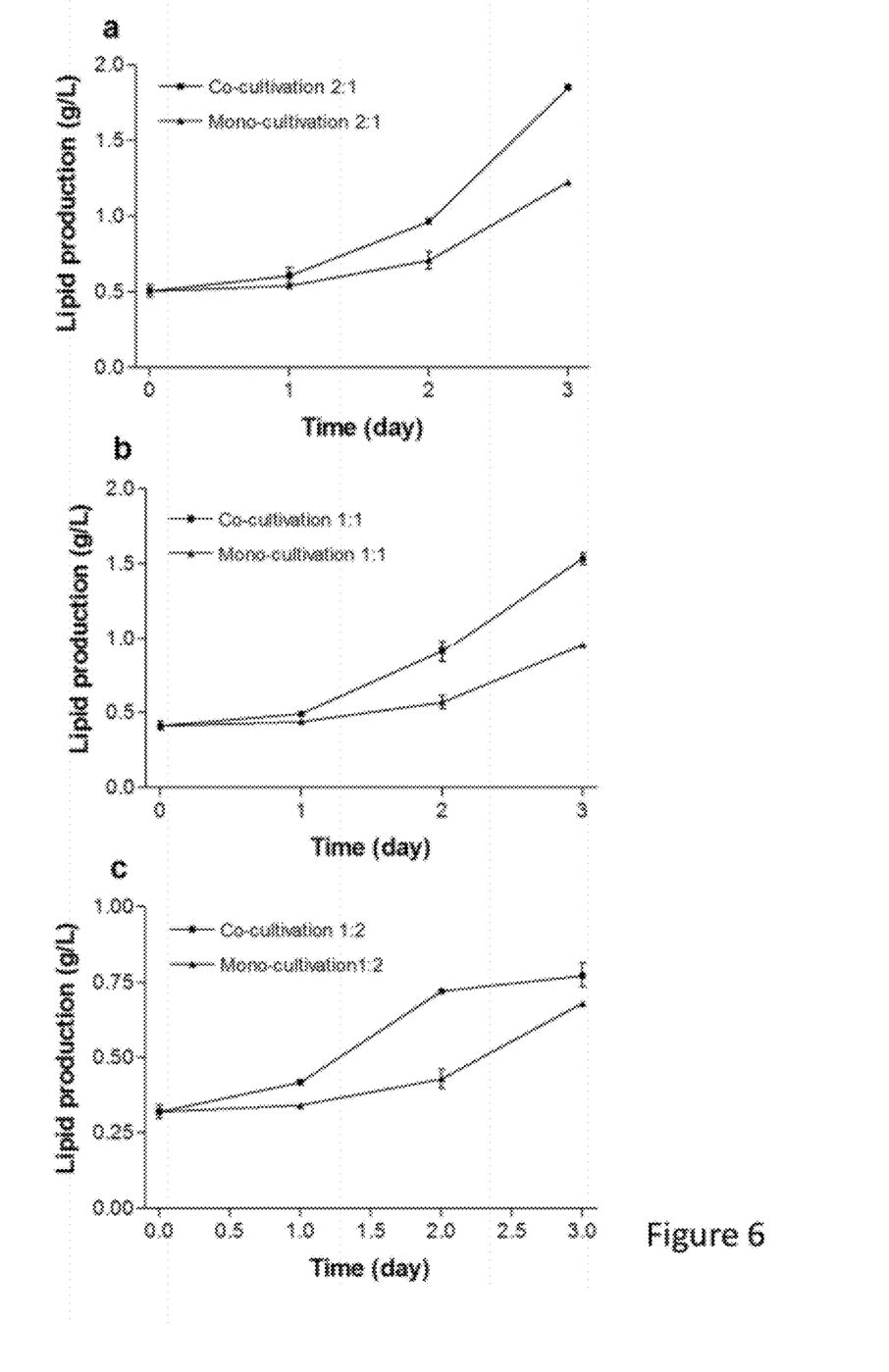

As demonstrated herein, pelletization can significantly improve the cultivation performance for higher yields of both lipid and biomass. Various evaluations of the cultivation performance for co-cultivation were performed. For example, as shown in FIG. 2A and FIG. 5, co-cultivation yielded an average of two to three folds of biomass as compared to the single cultivation. Considering that pelletization often greatly improves the fermentation performance for filamentous fungi, this result demonstrates that similar effects exist for the co-cultivation system. In addition to biomass, lipid production also increased (FIG. 2B and FIG. 6). The lipid profile by GC/MS reveals that co-cultivation did not change the lipid composition dramatically (FIG. 2C). In addition, Nile red staining imaging under confocal microscopy shows that the lipid body of the algae cells is still retaining its structure (FIGS. 1D-1F).

Figure 3:
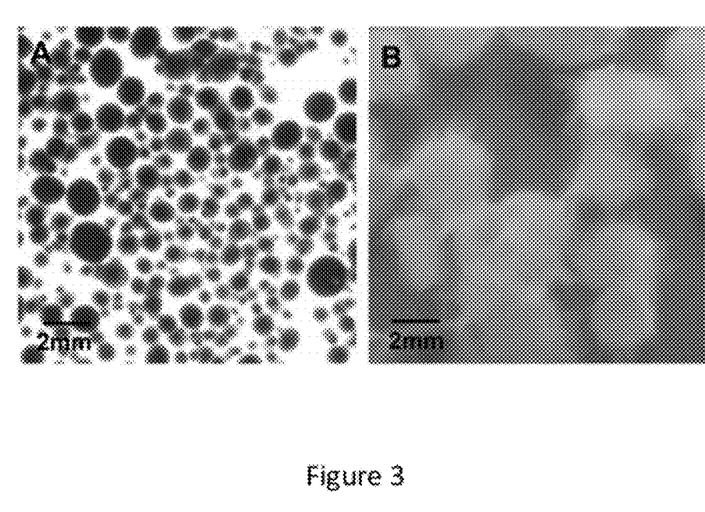

Further, the oleaginous fungi can secrete cellulase (FIG. 4B) to facilitate the usage of cell wall sugar from algae, which provides a synergistic improvement of cultivation performance and lipid production. As shown in FIG. 2C, scan electricity microscope observations reveal that part of the cell wall is being degraded while the algae still keeps its cell structure. More importantly, the cellulytic activity allows for selection of the proper fungal strains for sugar-free co-cultivation, where the cell wall sugar can be used to feed the fungal growth, and the fungi can grow in the sugar-free medium to form pellets with the algae, as depicted in FIG. 3.

Without being limited by any particular theory, it is believed that the observed increases in biomass could be due to several reasons. The removal of the algae from liquid culture may reduce the allelopathy impact to allow for the maximized utilization of the provided nutrient. This result is confirmed by sugar analysis, where most of the sugars in the liquid medium were used up in the co-cultivation as compared to the separate cultivation (FIG. 4C).

Another possible mechanism is the utilization of the cell wall carbonhydrate by the oleaginous fungi, which is supported by the observation of a slight increase of cellulase activity in the co-cultivation system, as well as the partial deconstruction of the algae cell wall. Even though biomass yield can increase up to three folds, the lipid yield increase is closer to about 1.5 folds. The difference is possibly due to the dramatic changes of pH for the liquid medium. As shown in FIG. 4D, the pH dropped dramatically during co-cultivation. Even though lower pH may be optimal for oleaginous fungi lipid production, algae generally achieves higher lipid yield at higher pH. The further increase of lipid may require a pH adjustment and the screening for algae strains producing high lipid yield at lower pH.

The co-cultivation system of the present invention represents a significant advance for algal biofuel technology, as the present invention provides for easier harvest of SCO microalgae, increased biomass and lipid yield. The present invention also dramatically decreases lipid and by-product production costs for microalgae. For example, co-cultivation provides an effective and low cost separation of algae from liquid medium using filtration. The co-cultivation platform can be readily integrated with both photobioreactors and raceway track systems, with only minor modifications of both growth systems. Further, the combination of different types of algae and fungi allow for production of a diverse range of products, from hydrocarbons to unsaturated fatty acids. Furthermore, many oleaginous fungi and algae species have been used for animal and fish feed, and thus the increased biomass may also serve as valuable by-products. By selecting strains and optimizing conditions, biomass and lipid yields will continue to increase. Lastly, the usage of a cellulytic fungal strain enables the pelletization without sugar-based preculture of filamentous fungi.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A system for the production of a biological product, comprising:
   at least one fungus;
   at least one algae; and
   a growth medium,
   wherein the at least one fungus and at least one algae are co-cultivated in or on the growth medium to form a pellet in or on the growth medium during co-cultivation, such that at least 50% of the co-cultivated algae is contained within the pellet, and wherein the pellet contains the biological product.

2. The system of claim 1, wherein the at least one fungus is from a class selected from the group consisting of Arthoniomycetes, Agaricomycetes, Blastocladiomycetes, Chytridiomycetes, Dacrymycetes, Dothideomycetes, Geoglossomycetes, Glomeromycetes, Eurotiomycetes, Lecanoromycetes, Leotiomycetes, Lichinomycetes, Monoblepharidomycetes, Orbiliomycetes, Sordariomycetes, Tremellomycetes, Pezizomycetes, Zygomycetes, and combinations thereof.

3. The system of claim 1, wherein the at least one algae is from a class selected from the group consisting of Actinochrysophyceae, Bacillariophyceae, Bryopsidophyceae, Bolidophyceae, Chlorarachnea, Chlorophyceae, Chrysophyceae, Cryptophyceae, Cyanophyceae, Diatomophyceae, Dinophyceae, Eustigmatophyceae, Glaucophyceae, Haptophyceae, Noctiluciphyceae, Pedinophyceae, Picophagophyceae, Pleurastrophyceae, Prasinophyceae, Prymnesiophyceae, Raphidophyceae, Synchromophyceae, Syndiniophyceae, Synurophyceae, Trebouxiophyceae, Ulvophyceae, Xanthophyceae, and combinations thereof.

4. The system of claim 3, wherein the at least one algae is from a genus selected from the group consisting of *Actinocyclus, Cyclotella, Cryptomonas, Monochrysis Chlorella, Chaetoceros, Haematococcus, Nannochloropsis, Pleurochrysis, Gracilaria, Sargassum, Dunaliella, Cyclotella, Navicula, Nitzschia, Spirulina, Phaeodactylum, Thalassiosira, Skeletonema, Porphyra* and combinations thereof.

5. The system of claim 1, wherein the biological product is selected from the group consisting of a biofuel, a biomass, a terpenoid compound, a bioplastic, a pigment, an antioxidant, a vitamin, an antibiotic, a surfactant protein, a peptide, a lipid, a therapeutic compound and combinations thereof.

6. The system of claim 5, wherein the terpenoid compound is selected from the group consisting of squalene, limonene, botryococcene and combinations thereof.

7. The system of claim 5, wherein the therapeutic compound is a neutraceutical.

8. The system of claim 7, wherein the neutraceutical is an unsaturated fatty acid including DHA and EPA.

9. The system of claim 5, wherein the therapeutic compound is a protein, peptide or lipid.

10. The system of claim 1, wherein the ratio of fungus to algae is about 1 to 1.

11. The system of claim 1, wherein the ratio of fungus to algae is about 2 to 1.

12. The system of claim 1, wherein the ratio of fungus to algae is about 1 to 2.

13. The system of claim 1, wherein the growth medium is selected from the group consisting of waste water, lignocellulosic biomass, corn, waste from bioethanol, biofuel production, waste from industrial processes and combinations thereof.

14. The system of claim 1, wherein the pellet has a diameter ranging between 0.2-15 mm.

* * * * *